United States Patent
Sivik et al.

(10) Patent No.: US 6,656,900 B2
(45) Date of Patent: Dec. 2, 2003

(54) COMPOSITIONS AND METHODS FOR USING AMINE OXIDE MONOMERIC UNIT-CONTAINING POLYMERIC SUDS ENHANCERS

(75) Inventors: Mark Robert Sivik, Mason, OH (US); Jean-Francois Bodet, Mason, OH (US); Bernard William Kluesener, Harrison, OH (US); William Michael Scheper, Lawrenceburg, IN (US); Dominic Wai-Kwing Yeung, Mississauga (CA); Vance Bergeron, Antony (FR)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/038,373

(22) Filed: Jan. 4, 2002

(65) Prior Publication Data

US 2003/0144167 A1 Jul. 31, 2003

(Under 37 CFR 1.47)

Related U.S. Application Data

(60) Provisional application No. 60/259,958, filed on Jan. 5, 2001.

(51) Int. Cl.$^7$ .............................. C11D 1/00; C11D 3/20; C11D 3/26; C11D 3/37
(52) U.S. Cl. ....................... 510/503; 510/237; 510/475; 510/505
(58) Field of Search ................................ 510/237, 475, 510/503, 505, 506

(56) References Cited

U.S. PATENT DOCUMENTS

| 3,457,312 | A |   | 7/1969  | Miller et al. |
| 4,297,251 | A | * | 10/1981 | Bernardino ................. 252/545 |
| 4,548,744 | A |   | 10/1985 | Connor et al. |
| 5,645,648 | A | * | 7/1997  | Laut et al. ..................... 134/2 |
| 5,776,878 | A |   | 7/1998  | Thoen et al. |
| 5,783,548 | A |   | 7/1998  | Fredj et al. |
| 6,554,007 | B2 | * | 4/2003 | Wise ....................... 134/22.14 |

FOREIGN PATENT DOCUMENTS

| EP | 0 595 383 A1 | 5/1994 |
| EP | 0 647 706 A2 | 4/1995 |
| EP | 0664 333 A1 | 7/1995 |
| WO | WO 9604358 A1 | 2/1996 |
| WO | WO 97/33963 | 9/1997 |
| WO | WO 00/71660 A1 | 11/2000 |

* cited by examiner

Primary Examiner—Gregory Delcotto
(74) Attorney, Agent, or Firm—Caroline Wei-Berk; Kim W. Zerby; Steve W. Miller

(57) ABSTRACT

The present invention relates to methods for using amine oxide monomer-containing polymeric suds enhancers (enhancers) to increase the suds and/or foam volume and suds and/or foam retention in suds-forming and/or foam-forming compositions comprising such amine oxide monomer-containing polymeric suds enhancers. Suitable suds-forming and/or foam-forming compositions comprise one or more amine oxide monomer-containing polymeric suds enhancers.

21 Claims, No Drawings

COMPOSITIONS AND METHODS FOR USING AMINE OXIDE MONOMERIC UNIT-CONTAINING POLYMERIC SUDS ENHANCERS

RELATED APPLICATIONS

This application claims priority under 35 U.S.C. §119(e) to U.S. Provisional Application No. 60/259,958, filed Jan. 5, 2001.

FIELD OF THE INVENTION

The present invention relates to methods for using amine oxide monomer-containing polymeric suds enhancers (suds boosters) to increase the suds and/or foam volume and suds and/or foam retention in suds-forming and/or foam-forming compositions comprising such amine oxide monomer-containing polymeric suds enhancers. Suitable suds-forming and/or foam-forming compositions comprise one or more amine oxide monomer-containing polymeric suds enhancers.

BACKGROUND OF THE INVENTION

Suds-forming and/or foam-forming compositions are well known. Such compositions require a suds-forming component and/or foam-forming component. Polymeric materials are one example of such suds-forming components and/or foam-forming components.

Formulators have been attempting unsuccessfully to develop better performing polymeric materials for use as suds-forming and/or foam-forming components.

Accordingly, there remains a need in the art for polymeric materials useful as suds-forming and/or foam-forming components suitable for suds-forming and/or foam-forming compositions which exhibit increased suds and/or foam volume and suds and/or foam retention. The need exists for a composition which can maintain a high level of suds and/or foam as long as the suds-forming and/or foam-forming composition is effective for its purpose.

SUMMARY OF THE INVENTION

The present invention meets the aforementioned needs in that it has been surprisingly discovered that certain amine oxide monomer-containing polymeric materials serve as suds and/or foam extenders and suds and/or foam volume enhancers in suds-forming and/or foam-forming compositions.

The amine oxide monomer-containing polymeric suds enhancers of the present invention comprise monomeric units which have at least one moiety capable of sustaining a negative charge at a pH of from about 4 to about 12 and at least one moiety capable of sustaining a positive charge within the same pH range.

The present invention relates to a method for providing increased suds volume and increased suds retention in suds-forming and/or foam-forming compositions such as liquid dishwashing compositions, personal care compositions (i.e., shampoos, hand washing compositions, body washing composition, hair removal compositions, etc.), laundry detergent compositions, especially laundry bars and/or high suds phosphate laundry compositions, hard surface cleaning compositions, agrochemical foaming compositions, oil-field foaming compositions and/or fire-firefighting foaming compositions.

In one aspect, a method for providing increased suds volume and increased suds retention while washing, especially by hand, dishware (dishware being defined as any hard surface object on which, in which and/or from which a food or beverage is served, stored or cooked) in need of cleaning, comprising the step of contacting said dishware with an aqueous solution of a liquid dishwashing composition, said liquid dishwashing composition comprising:
 a) an effective amount of a amine oxide monomer-containing polymeric suds enhancer as hereinafter defined;
 b) an effective amount of a detersive surfactant; and
 c) balance carriers and other adjunct ingredients;
 provided that the pH of a 10% aqueous solution of said liquid dishwashing composition is from about 4 to about 12, is provided.

In another aspect, a method for providing increased suds volume and increased suds retention while washing parts of a person's body, such as hair, hands, other parts of the body, in need of cleaning, comprising the step of contacting said parts with an aqueous solution of a personal care composition, said personal care composition comprising:
 a) an effective amount of a amine oxide monomer-containing polymeric suds enhancer as hereinafter defined;
 b) an effective amount of a detersive surfactant; and
 c) balance carriers and other adjunct ingredients;
 provided that the pH of a 10% aqueous solution of said personal care composition is from about 4 to about 12, is provided.

In another aspect, a method for providing increased suds volume and increased suds retention while washing, preferably by hand, a fabric and/or garment in need of cleaning, comprising the step of contacting said fabric and/or garment with an aqueous solution of a laundry detergent composition, said laundry detergent composition comprising:
 a) an effective amount of a polymeric suds enhancer as hereinafter defined;
 b) an effective amount of a detersive surfactant; and
 c) balance carriers and other adjunct ingredients;
 provided that the pH of a 10% aqueous solution of said laundry detergent composition is from about 4 to about 12, is provided.

In yet another aspect, a method for providing increased suds volume and increased suds retention while cleaning a hard surface, such as a countertop, tile floors, bathroom fixtures, bathtubs, showers, toilets, etc., in need of cleaning in need of cleaning, comprising the step of contacting said hard surface with an aqueous solution of a hard surface cleaning composition, said hard surface cleaning composition comprising:
 a) an effective amount of a polymeric suds enhancer as hereinafter defined;
 b) an effective amount of a detersive surfactant; and
 c) balance carriers and other adjunct ingredients;
 provided that the pH of a 10% aqueous solution of said hard surface cleaning composition is from about 4 to about 12, is provided.

In still yet another aspect, a method for providing increased suds volume and increased suds retention while treating a plant and/or crop in need of treatment, comprising the step of contacting said plant and/or crop with an aqueous solution of a agrochemical foaming composition, said agrochemical foaming composition comprising:
 a) an effective amount of a polymeric suds enhancer as hereinafter defined;

b) an effective amount of a detersive surfactant; and c) balance carriers and other adjunct ingredients;

provided that the pH of a 10% aqueous solution of said agrochemical foaming composition is from about 4 to about 12, is provided.

In still yet another aspect, a method for providing increased suds volume and increased suds retention while drilling for oil in oil-fields, comprising the step of contacting said drilling equipment and/or subterranean formations with an aqueous solution of a oil-field foaming composition, said oil-field foaming composition comprising:

a) an effective amount of a polymeric suds enhancer as hereinafter defined;

b) an effective amount of a clay; and c) balance carriers and other adjunct ingredients;

provided that the pH of a 10% aqueous solution of said oil-field foaming composition is from about 4 to about 12, is provided.

In still yet another aspect, a method for providing increased suds volume and increased suds retention while fighting a fire, comprising the step of contacting said fire with an aqueous solution of a fire-fighting foaming composition, said fire-fighting foaming composition comprising:

a) an effective amount of a polymeric suds enhancer as hereinafter defined;

b) an effective amount of a detersive surfactant; and c) balance carriers and other adjunct ingredients;

provided that the pH of a 10% aqueous solution of said fire-fighting foaming composition is from about 4 to about 12, is provided.

The present invention also relates to the suds and/or foam forming compositions and/or suds and/or foam retention compositions used in the methods described herein.

These and other objects, features and advantages will become apparent to those of ordinary skill in the art from a reading of the following detailed description and the appended claims.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

"Effective amount of a polymeric suds enhancer (suds booster)"—An "effective amount of a polymeric suds enhancer (suds booster)" as used herein means a sufficient amount of the polymeric suds enhancer such that greasy and/or composite soils are removed and/or reduced from a substrate coming into contact with the polymeric suds enhancer.

The present invention relates to amine oxide monomer-containing polymeric materials which provide enhanced suds and/or foam duration and enhanced suds and/or foam volume when formulated into suds-forming and/or foam-forming compositions. The amine oxide polymers of the present invention may be homopolymers or copolymers, each of which may be suitably crosslinked. The amine oxide polymers are comprised of moieties which when placed in an aqueous solution having a pH of form 4 to about 12, said moieties are capable of sustaining a positive or negative charge.

The suds-forming and/or foam-forming compositions of the present invention have a pH of from about 4 to about 12 when measured as a 10% aqueous solution. The polymeric suds enhancers of the present invention are amine oxide polymers. For the purposes of the present invention the term "amine oxide polymer" is defined as "a polymeric material comprised of one or more monomers wherein each monomer has one or more moieties capable of sustaining a positive or negative charge at a pH of from about 4 to about 12 such that the number of positively charged moieties is equal to the number of negatively charged moieties at the isoelectric point of said polymer."

The compositions according to the present invention also comprise an effective amount of one or more detersive surfactants described herein below as well as carriers and other adjunct ingredients.

The suds-forming and/or foam-forming compositions of the present invention comprise:

a) an effective amount of a amine oxide monomer-containing polymeric suds enhancer; and b) optionally an effective amount of a detersive surfactant or clay; and c) the balance carriers and other adjunct ingredients;

provided that a 10% aqueous solution of said composition has a pH of from about 4 to about 12.

The following describe non-limiting examples of polymeric material which may be suitable for use in the suds-forming and/or foam-forming compositions of the present invention.

Polymeric Suds Enhancers

Amine Oxide Monomeric Units

The polymeric suds enhancers of the present invention are preferably homopolymers or copolymers.

The polymeric suds enhancers of the present invention comprise an amine oxide monomeric unit having the formula:

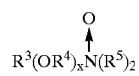

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

In addition to the amine oxide monomer unit, the polymeric suds enhancers of the present invention may comprise one or more other monomeric units as described below.

A preferred class of amine oxide monomer units suitable for use as a polymeric suds volume and suds duration enhancer has the formula:

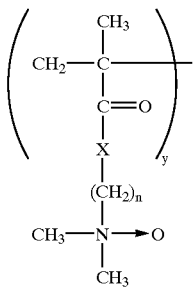

wherein X is either O or N, n is an integer from 1 to 10, preferably from 2 to 6, more preferably 2 to 4.

The polymeric suds enhancers (suds boosters) of the present invention preferably have a molecular weight in the range of from about 1,000 to about 2,000,000, preferably from about 5,000 to about 1,000,000, more preferably from about 10,000 to about 750,000, more preferably from about 10,000 to about 500,000, even more preferably from about 15,000 to about 300,000 daltons. Most preferably, the molecular weight of the polymeric suds enhancers is about 50,000 daltons or less.

The molecular weight of the polymeric suds enhancers of the present invention are determined using a Gel Filtration Chromatography (GFC) Method. Under this GFC Method, polymers are separated using GFC columns to determine molecular weight distribution. The molecular weight and distributions are measured through separation of the polymer species based on their hydrodynamic volumes. The hydrodynamic volume is related to molecular weight.

A detailed example of how the molecular weights of the polymeric suds enhancers of the present invention are determined follows. A 0.2% solution of the polymeric suds enhancer is first prepared in the aqueous mobile phase, 80/20 0.5M Ammonium Acetate/Methanol at pH 3.7. The solution is then injected onto the GFC column at 60° C. and its absolute molecular weight and molecular weight distribution are calculated using both multi-angle laser light scattering (MALLS) and refractive index (RI) detection. Theoretical and practical examples of molecular weights determined by the GFC Method are found in: W. W. Yau, J. J. Kirkland, and D. D. Bly, *Modern Size-Exclusion Liquid Chromatography*, John Wiley & Sons, New York, 1979.

Other Monomers

In addition to the amine oxide monomeric units, the suds enhancers of the present invention may, and preferably do include one or more other monomeric units, other than amine oxide monomeric units, such as quaternary nitrogen-containing monomeric units and zwitterionic monomeric units, other cationic monomeric units, hydroxyl-containing monomeric units, hydrophobic monomeric units, hydrophilic monomeric units, anionic monomeric units and nonionic monomeric units.

Quaternary Nitrogen-Containing Monomeric Units

Any suitable quaternary nitrogen-containing group can be used as a monomeric unit of the polymeric suds enhancers of the present invention.

Nonlimiting examples of quaternary nitrogen-containing monomeric units suitable for the polymeric suds enhancers of the present invention include:

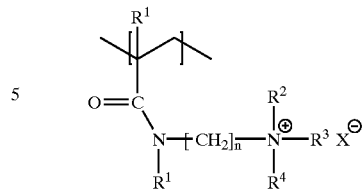

wherein $R^1$ is a hydrogen or a methyl group, preferably a methyl group; $R^2$, $R^3$ and $R^4$ are linear or branched $C_1$–$C_4$ alkyl groups, preferably $C_1$ groups; n represents an integer from 1 to 4, preferably 3; and $X^-$ represents a counterion which is compatible with the water-soluble or water-dispersible nature of the polymer, preferably $Cl^-$;

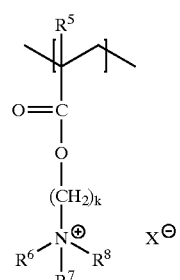

wherein $R^5$, $R^6$, $R^7$ and $R^8$ are independently H, or a $C_1$–$C_4$ alkyl group, preferably a methyl group; k is an integer from 1 to 4, preferably 2; and $X^-$ represents a counterion which is compatible with the water-soluble or water-dispersible nature of the polymer, preferably $Cl^-$; and

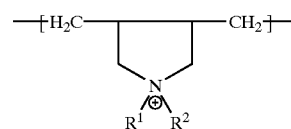

wherein $R^1$ and $R^2$ are independently H or a $C_1$–$C_4$ alkyl group, preferably a methyl group.

Zwitterionic Units

Any suitable zwitterionic group can be used as a monomeric unit of the suds enhancers of the present invention.

Nonlimiting examples of zwitterionic monomeric units suitable for the suds enhancers of the present invention include:

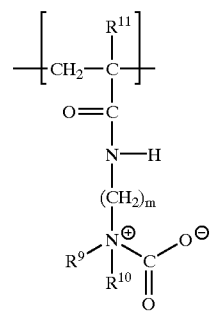

wherein $R^9$, $R^{10}$ and $R^{11}$ are independently H, or a $C_1$–$C_4$ alkyl group, preferably a methyl group; and m is an integer from 1 to 4, preferably 2.

Nonlimiting examples of zwitterionic monomeric units in accordance with the present invention include:

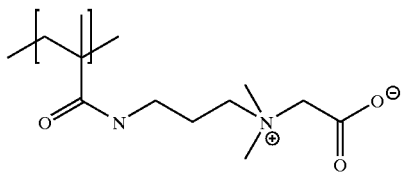

Cationic Monomeric Units

For the purposes of the present invention the term "cationic monomeric unit" is defined as "a moiety which when incorporated into the structure of the suds enhancers of the present invention, is capable of maintaining a cationic charge within the pH range of from about 4 to about 12. The cationic monomeric unit is not required to be protonated at every pH value within the range of about 4 to about 12." Non-limiting examples of monomeric units which comprise a cationic moiety, other than a quaternary nitrogen-containing moiety, include the cationic monomeric units having the formula:

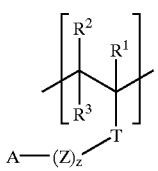

[I]

wherein each of $R^1$, $R^2$ and $R^3$ are independently selected from the group consisting of hydrogen, $C_1$ to $C_6$ alkyl, and mixtures thereof, preferably hydrogen, $C_1$ to $C_3$ alkyl, more preferably, hydrogen or methyl. T is selected from the group consisting of substituted or unsubstituted, saturated or unsaturated, linear or branched radicals selected from the group consisting of alkyl, cycloalkyl, aryl, alkaryl, aralkyl, heterocyclic ring, silyl, nitro, halo, cyano, sulfonato, alkoxy, keto, ester, ether, carbonyl, amido, amino, glycidyl, carbanato, carbamate, carboxylic, and carboalkoxy radicals and mixtures thereof. Z is selected from the group consisting of: —(CH$_2$)—, (CH$_2$—CH=CH)—, —(CH$_2$—CHOH)—, (CH$_2$—CHNR$^4$)—, —(CH$_2$—CHR$^5$—O)— and mixtures thereof, preferably —(CH$_2$)—. $R^4$ and $R^5$ are selected from the group consisting of hydrogen, $C_1$ to $C_6$ alkyl and mixtures thereof, preferably hydrogen, methyl, ethyl and mixtures thereof; z is an integer selected from about 0 to about 12, preferably about 2 to about 10, more preferably about 2 to about 6. A is NR$^6$R$^7$ or NR$^6$R$^7$R$^8$. Wherein each of R$^6$, R$^7$ and R$^8$, when present, are independently selected from the group consisting of H, $C_1$–$C_8$ linear or branched alkyl, alkyleneoxy having the formula:

—(R$^9$O)$_y$R$^{10}$ wherein $R^9$ is $C_2$–$C_4$ linear or branched alkylene, and mixtures thereof; $R^{10}$ is hydrogen, $C_1$–$C_4$ alkyl, and mixtures thereof; y is from 1 to about 10. Preferably R$^6$, R$^7$ and R$^8$, when present, are independently, hydrogen, $C_1$ to $C_4$ alkyl. Alternatively, NR$^6$R$^7$ or NR$^6$R$^7$R$^8$ can form a heterocyclic ring containing from 4 to 7 carbon atoms, optionally containing additional hetero atoms, optionally fused to a benzene ring, and optionally substituted by $C_1$ to $C_8$ hydrocarbyl, and/or acetates. Examples of suitable heterocycles, both substituted and unsubstituted, are indolyl, isoindolinyl imidazolyl, imidazolinyl, piperidinyl pyrazolyl, pyrazolinyl, pyridinyl, piperazinyl, pyrrolidinyl, pyrrolidinyl, guanidino, amidino, quinidinyl, thiazolinyl, morpholine and mixtures thereof, with morpholino and piperazinyl being preferred.

Examples of the cationic unit of formula [I] include, but are not limited to, the following structures:

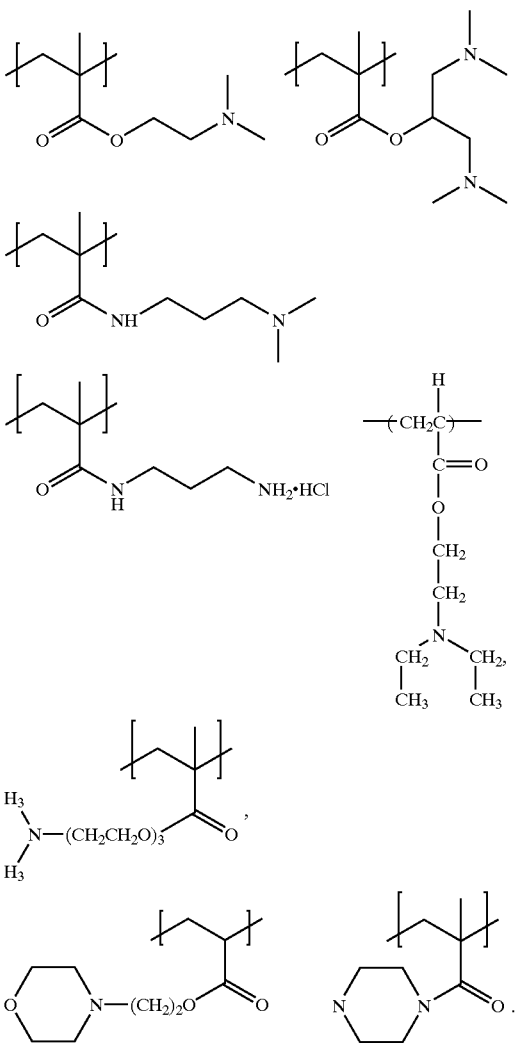

A preferred cationic monomeric unit is 2-dimethylaminoethyl methacrylate (DMAM) having the formula:

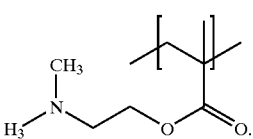

Nonlimiting examples of cationic monomeric units include: methyl chloride quats of dimethylethyl(meth)acrylates, methyl chloride quats of dimethylaminopropyl (meth)acrylamides, dimethyl- and diethylsulfate quats of dimethylaminoethyl(meth)acrylates, dimethyl- and diethylsulfate quats of dimethylaminopropyl(meth)acrylamides, and diallydimethylammonium halides, such as bromide and/or chloride salts.

Hydroxyl-Containing Monomeric Units

The hydroxyl group density of a quaternary nitrogen-containing monomer- and/or zwitterionic monomer-containing polymeric suds enhancer of the present invention is determined by the following calculation.

$$\text{Hydroxyl Group Density} = \frac{[\text{Molecular Weight of Hydroxyl Group}]}{[\text{Total Monomer Molecular Weight}]}$$

For example, the Hydroxyl Group Density of a quaternary nitrogen-containing monomer- and/or zwitterionic monomer-containing polymeric suds enhancer containing 2-dimethylaminoethyl methacrylate having a molecular weight of approximately 157 and hydroxyethylacrylate having a molecular weight of approximately 116 grams/mole, at a 1:3 mole ratio would be calculated as follows:

$$\text{Hydroxyl Group Density} = \frac{[17]}{[3(116) + 157]} = 0.0337$$

Preferably, the quaternary nitrogen-containing or zwitterionic polymeric suds enhancers of the present invention have a Hydroxyl Group Density of about 0.5 or less, preferably from about 0.0001 to about 0.4.

Nonlimiting examples of such hydroxyl group-containing units include, but are not limited to the following:

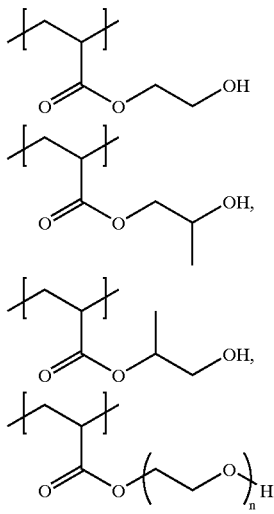

wherein n is an integer from 2 to 100, preferably 2 to 50, more preferably 2 to 30,

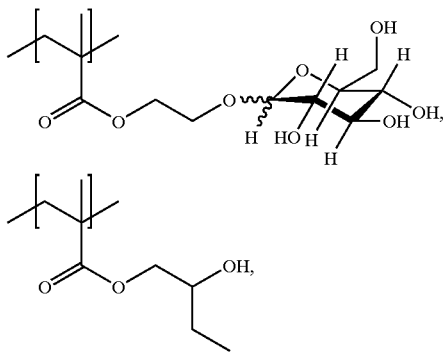

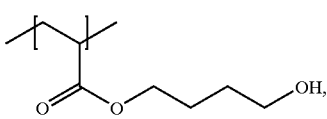

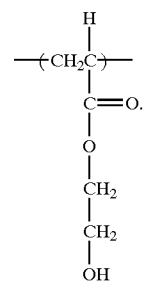

Hydrophobic Group-Containing Monomeric Units

Suitable hydrophobic group-containing monomeric units for use in the present invention include, but are not limited to, hydrophobic groups preferably selected from the group consisting of non-hydroxyl groups, non-cationic groups, non-anionic groups, non-carbonyl groups, and/or non-H-bonding groups, more preferably selected from the group consisting of alkyls, cycloalkyls, aryls, alkaryls, aralkyls and mixtures thereof.

Nonlimiting examples of such hydrophobic group-containing monomeric units include, but are not limited to the following:

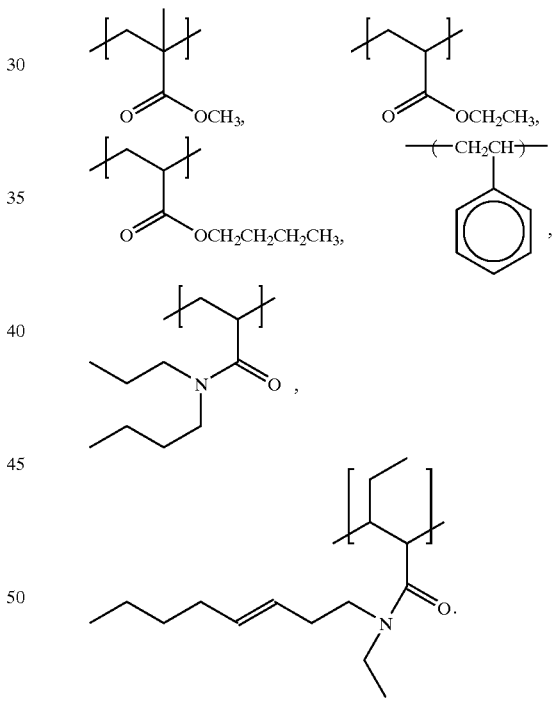

Hydrophilic Group-Containing Monomeric Units

Suitable hydrophilic group-containing monomeric units for use in the present invention include, but are not limited to, hydrophilic groups preferably selected from the group consisting of carboxyl groups, carboxylic acids and their salts, sulfonic acids and their salts, heteroatom-containing moieties present in a ring or linear form and mixtures thereof.

Nonlimiting examples of such hydrophilic group-containing monomeric units include, but are not limited to the following:

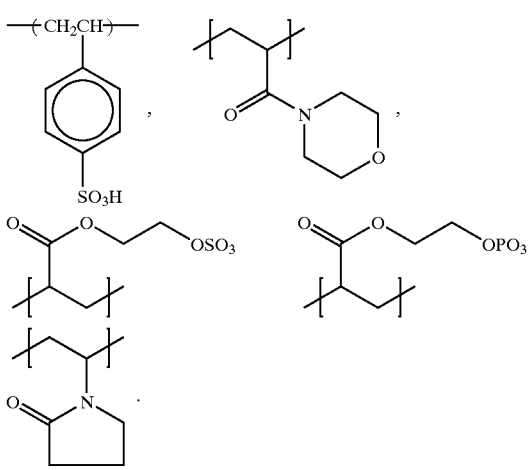

Anionic Monomeric Units

For the purposes of the present invention the term "anionic monomeric unit" is defined as "a moiety which when incorporated into the structure of the suds enhancers of the present invention, is capable of maintaining an anionic charge within the pH range of from about 4 to about 12. The anionic monomeric unit is not required to be de-protonated at every pH value within the range of about 4 to about 12." Nonlimiting examples of anionic monomeric units include: acrylic acid, methacrylic acid, AMPS, vinyl sulfonate, styrene vinyl sulfonate, vinyl phosphonic acid, ethylene glycol methacrylate phosphate, maleic anhydride and acid, fumaric acid, itaconic acid, glutamic acid, aspartic acid, the monomeric unit having the formula:

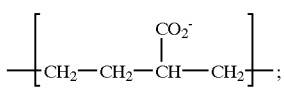

and the monomeric unit having the formula:

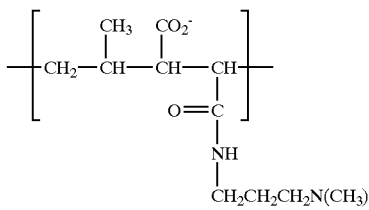

the latter of which also comprises a moiety capable of having a cationic charge at a pH of about 4 to about 12. This latter unit is defined herein as "a unit capable of having an anionic and a cationic charge at a pH of from about 4 to about 12."

Nonionic Monomeric Units

For the purposes of the present invention the term "nonionic monomeric unit" is defined as "a moiety which when incorporated into the structure of the suds enhancers of the present invention, has no charge within the pH range of from about 4 to about 12." Non-limiting examples of units which are "nonionic monomeric units" are styrene, ethylene, propylene, butylene, 1,2-phenylene, esters, amides, ketones, ethers, acrylamide and the N-monosubstituted—(e.g., N-isopropylacrylamide) and N,N-disubstituted (e.g., N,N-dimethylacrylamide) acrylamides, hydroxyethyl(meth)acrylate, hydroxypropyl(meth)acrylate, vinyl pyrrolidone, alkyl substituted alkoxylated (meth)acrylate, dimethylaminoethyl(meth)acrylate, dimethylaminopropyl (meth)acrylamide, vinyl formamide and the like.

The units which comprise the polymers of the present invention may, as single units or monomers, have any $pK_a$ value.

Preferably, the quaternary nitrogen-containing monomer- or zwitterionic monomer-containing polymeric suds enhancers are selected from copolymers, which can optionally be crosslinked, terpolymers and other polymers (or multimers).

Particular Polymers

Preferred polymers of the present invention comprise:

A. at least one monomeric unit selected from the group consisting of:
(i) amine oxide monomeric units having the formula:

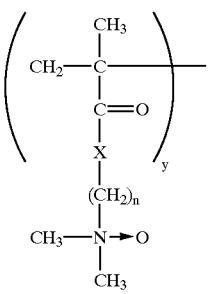

wherein X is either O or N, n is an integer from 1 to 10, preferably from 2 to 6, more preferably 2 to 4.

B. optionally, at least one cationic monomeric unit having a formula:

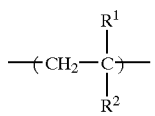

wherein:
$R^1$ is H or an alkyl having 1 to 10 carbon atoms,
$R^2$ is a moiety selected from the group consisting of

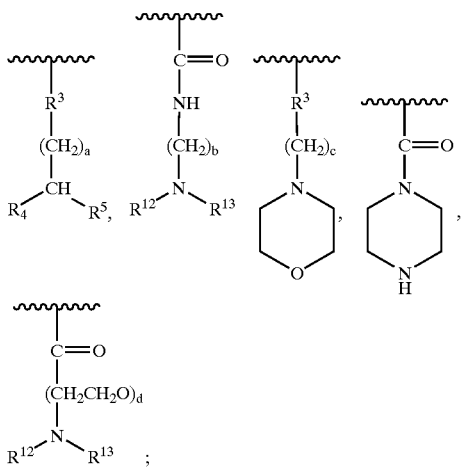

wherein $R^3$ is selected from the group consisting of
a is an integer from 0 to 16, preferably 0 to 10;

—O—, $$-\overset{O}{\underset{\|}{C}}-$$

b is an integer from 2 to 10;
c is an integer from 2 to 10;
d is an integer from 1 to 100;
$R^4$ and $R^5$ are independently selected from the group consisting of —H, and $$—R^8—N\begin{matrix}R^9\\ \\R^1\end{matrix}$$

$R^8$ is independently selected from the group consisting of a bond or an alkylene having 1 to 18 carbon atoms;
$R^9$ and $R^{10}$ are independently selected from the group consisting of —H, alkyl having 1 to 8 carbon atoms, and an olefin chain having 2 to 8 carbon atoms;
$R^{12}$ and $R^{13}$ are independently selected from the group consisting of H and alkyl having from 1 to 8 carbon atoms;

[structure with C=O, O, (CH₂)ₓ, piperazine and morpholine rings]

wherein x is an integer from 2 to 10;
C. optionally, at least one monomeric unit selected from the group consisting of:
a monomeric unit of the formula:

$$-(CH_2-\underset{R^{21}}{\overset{R^{20}}{C}})-$$

wherein $R^{20}$ is selected from the group consisting of H and $CH_3$;
$R^{21}$ is selected from the group consisting of:

[structures: morpholine C=O, pyrrolidone, ester with CH₃, OH]

$$\overset{\xi}{\underset{\xi}{\big\{}}-\overset{O}{\underset{\|}{C}}-O-(CH_2)_e-OH;$$

wherein e is an integer from 2 to 25, preferably from 2 to 5;

—O—(CH₂)f—CH₃ wherein f is an integer from 0 to 25, preferably from 0 to 12;

$$-\overset{O}{\underset{\|}{C}}-O-(\overset{R^{23}}{\underset{|}{CH}}CH_2O)_g—$$
$$-\overset{O}{\underset{\|}{C}}-O-(CH_2\overset{R^{24}}{\underset{|}{CH}}O)_h—\ ;$$

wherein g is an integer from 1 to 100, preferably 1 to 50;
wherein h is an integer from 1 to 100, preferably 1 to 50;
$R^{23}$ is —H, —$CH_3$ or —$C_2H_5$;
$R^{24}$ is —$CH_3$ or —$C_2H_5$;

$$-\overset{O}{\underset{\|}{C}}-\underset{H}{N}-(\underset{R''}{\overset{|}{CR'}})_j-OH;$$

wherein R' and R'' are independently H or $CH_3$; and j is an integer from 1 to 25, preferably 2 to 12;

$$-\overset{O}{\underset{\|}{C}}-\underset{H}{N}-CH_2-\underset{|}{\overset{CH_3}{CH}}-O;$$

[structure with C=O, O, (CH₂)k, and sugar ring with OH groups]

wherein k is an integer from 1 to 25, preferably 1 to 12;

[benzene ring with SO₃H]

—NH—(CH₂)ₘ—NH₂·HCl, wherein m is an integer from 1 to 25, preferably 2 to 12; and
a polyhydroxy monomeric unit of formula:

$$—O—(\underset{|}{\overset{OH}{CH}}—\underset{|}{\overset{OH}{CH}})_n—$$

wherein n is an integer from 1 to 50, preferably 1 to 25; and

D. optionally at least one monomeric unit selected from the group consisting of:

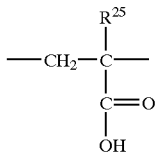

wherein $R^{25}$ is —H or —CH$_3$;

wherein $R^{26}$ is —H.

A preferred terpolymer and/or multimer of the present invention comprises at least one said monomeric unit A, at least one said monomeric unit B and at least one said monomeric unit C.

Preferably, at least one monomeric unit B is selected from the group consisting of:

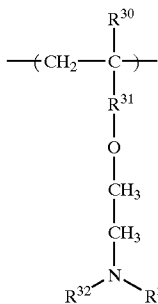

wherein $R^{30}$ is H or —CH$_3$,
wherein $R^{31}$ is a bond or

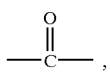

, and
$R^{32}$ and $R^{33}$ are —CH$_3$ or —C$_2$H$_5$.

Preferably, the polymer is a terpolymer in which:
said at least one monomeric unit C is selected from the group consisting of:

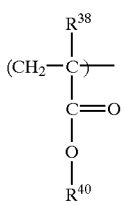

wherein $R^{38}$ is selected from the group consisting of H and CH$_3$ and
$R^{40}$ is selected from the group consisting of —CH$_2$CH$_2$—OH and

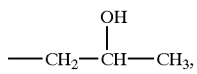

and isomers thereof; and
said terpolymer comprising said at least one monomeric unit D.

Preferably, the polymer has at least one monomeric unit C which has the formula:

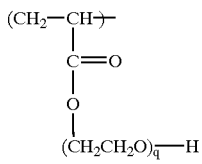

wherein q ranges from 1 to 12, preferably 1 to 10, more preferably 1 to 9.

Preferably, the polymer is a terpolymer, in which at least one monomeric unit B is selected from the group consisting of:

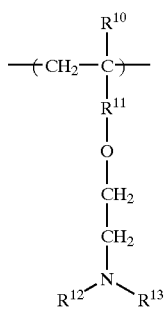

wherein $R^{10}$ is H or CH$_3$;

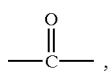

$R^{11}$ is a bond or, and $R^{12}$ and $R^{13}$ are —CH$_3$ or —C$_2$H$_5$, and said polymer comprises said at least one monomeric unit D.

Preferably, at least one monomeric unit B has a formula selected from the group consisting of:

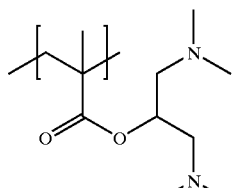

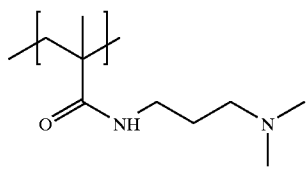

Preferably, at least one monomeric unit B has a formula selected from the group consisting of:

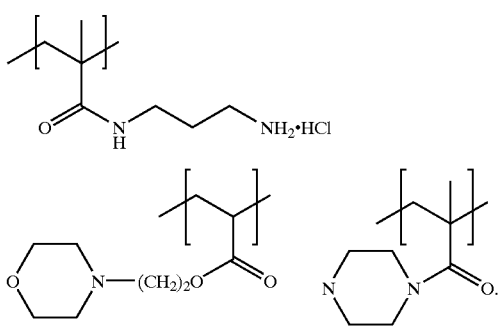

Preferably, at least one one monomeric unit C is selected from the group consisting of:

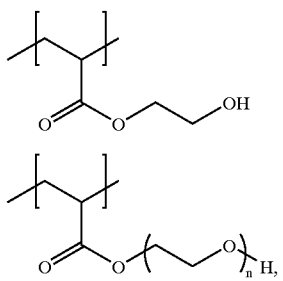

wherein n is an integer from 2 to 50, preferably 2 to 30, more preferably 2 to 27;

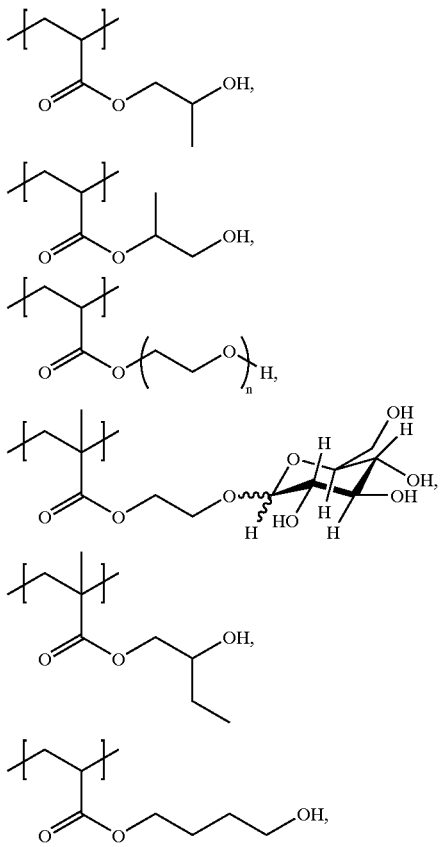

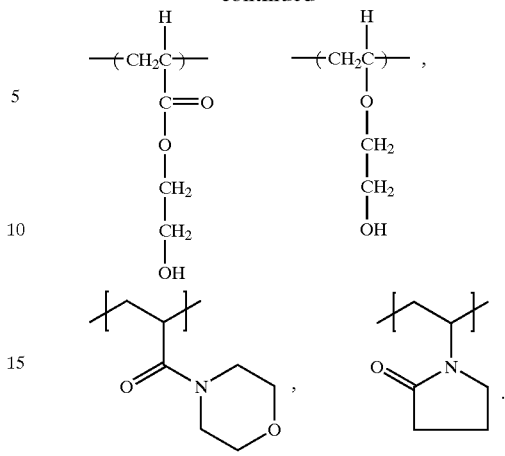

Specific Polymers

Nonlimiting examples of amine oxide monomeric unit-containing polymers, copolymers, which can optionally be cross-linked, homopolymers, terpolymers and/or multimers of the present invention have the following formulas:

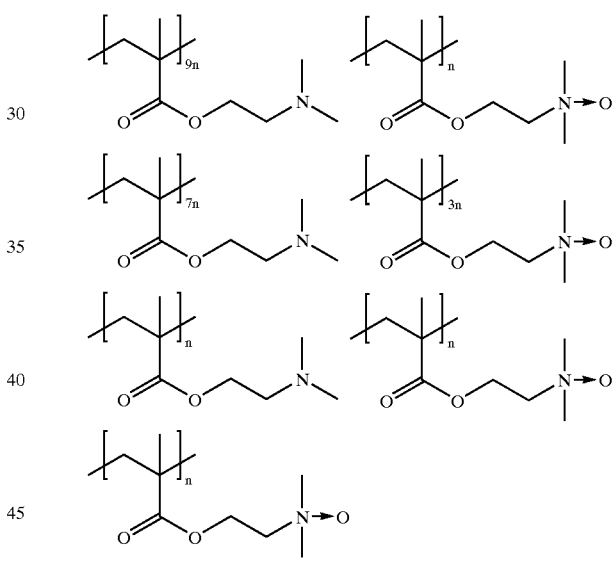

Preferred examples of amine oxide monomeric unit-containing polymers of the present invention include:

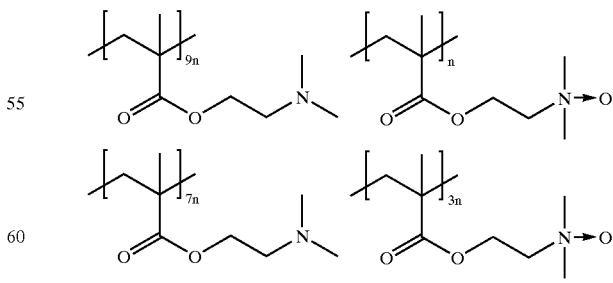

Methods of Use

The present invention relates to a method for providing increased suds volume and increased suds retention in suds-forming and/or foam-forming compositions, such as liquid dishwashing compositions, personal care compositions (i.e., shampoos, hand washing compositions, body washing composition, hair removal compositions, etc.), laundry detergent compositions, especially laundry bars and/or high suds phosphate laundry compositions, hard surface cleaning compositions, agrochemical foaming compositions, oil-field foaming compositions and/or fire-firefighting foaming compositions.

Liquid Dishwashing Compositions

The liquid detergent compositions according to the present invention comprise at least an effective amount of one or more amine oxide monomeric unit-containing suds enhancers described herein, preferably from about 0.01% to about 10%, more preferably from about 0.001% to about 5%, most preferably from about 0.1% to about 2% by weight, of said composition and optionally, but typically, the balance comprising one or more cleaning adjuncts. Nonlimiting examples of suitable cleaning adjuncts include surfactants including diamines, amine oxides, betaines and/or sultaines, enzymes, builders, solvents such as water and/or other carriers, hydrotropes, calcium and/or magnesium ion-containing materials, pH agents, perfumes, chelants, soil release polymers, polymeric dispersants, polysaccharides, abrasives, bactericides, tarnish inhibitors, opacifiers, dyes, buffers, antifungal or mildew control agents, thickeners, processing aids, suds boosters, brighteners, anti-corrosive aids, stabilizers, antioxidants and other suitable adjuncts known by those of ordinary skill in the art.

The compositions of this invention can be used to form aqueous washing solutions for use in hand dishwashing. Generally, an effective amount of such compositions is added to water to form such aqueous cleaning or soaking solutions. The aqueous solution so formed is then contacted with the dishware, tableware, and cooking utensils.

An effective amount of the detergent compositions herein added to water to form aqueous cleaning solutions can comprise amounts sufficient to form from about 500 to 20,000 ppm of composition in aqueous solution. More preferably, from about 800 to 5,000 ppm of the detergent compositions herein will be provided in aqueous cleaning liquor.

The liquid dishwashing compositions of the present invention also provide a means for preventing the redeposition of grease, oils, and dirt, especially grease, from the hand washing solution onto dishware. This method comprises contacting an aqueous solution of the compositions of the present invention with soiled dishware and washing said dishware with said aqueous solution.

An effective amount of the detergent compositions herein added to water to form aqueous cleaning solutions according to the method of the present invention comprises amounts sufficient to form from about 500 to 20,000 ppm of composition in aqueous solution. More preferably, from about 800 to 2,500 ppm of the detergent compositions herein will be provided in aqueous cleaning liquor.

The liquid detergent compositions of the present invention are effective for preventing the redeposition of grease from the wash solution back onto the dishware during washing. One measure of effectiveness of the compositions of the present invention involves redeposition tests. The following test and others of similar nature are used to evaluate the suitability of the formulas described herein.

A polyethylene 2 L graduated cylinder is filled to the 1 L graduation mark with an aqueous (water=7 grain) solution comprising from about 500 to about 20,000 ppm of a liquid detergent composition according to the present invention. A synthetic greasy soil composition is then added to the cylinder and the solution is agitated. After a period of time the solution is decanted from the graduated cylinder and the interior walls of the graduated cylinder are rinsed with a suitable solvent or combination of solvents to recover any re-deposited greasy soil. The solvent is removed and the weight of greasy soil which remains in solution is determined by subtracting the amount of soil recovered from the amount initially added to the aqueous solution.

Other re-deposition test include immersion of tableware, flatware, and the like and recovering any re-deposited soil.

The above test can be further modified to determine the increased amount of suds volume and suds duration. The solution is first agitated then subsequently challenged with portions of greasy soil with agitation between each subsequent soil addition. The suds volume can be easily determined by using the vacant volume of the 2 L cylinder as a guide.

Non-Aqueous Liquid Detergents

The manufacture of liquid detergent compositions which comprise a non-aqueous carrier medium can be prepared according to the disclosures of U.S. Pat. Nos. 4,753,570; 4,767,558; 4,772,413; 4,889,652; 4,892,673; GB-A-2,158, 838; GB-A-2,195,125; GB-A-2,195,649; U.S. Pat. No. 4,988,462; U.S. Pat. No. 5,266,233; EP-A-225,654 (Jun. 16, 1987); EP-A-510,762 (Oct. 28, 1992); EP-A-540,089 (May 5, 1993); EP-A-540,090 (May 5, 1993); U.S. Pat. No. 4,615,820; EP-A-565,017 (Oct. 13, 1993); EP-A-030,096 (Jun. 10, 1981), incorporated herein by reference. Such compositions can contain various particulate detersive ingredients stably suspended therein. Such non-aqueous compositions thus comprise a LIQUID PHASE and, optionally but preferably, a SOLID PHASE, all as described in more detail hereinafter and in the cited references.

Other Compositions

In addition to liquid detergent compositions, an effective amount of one or more amine oxide monomeric unit-containing suds enhancers can be used in other compositions such as personal care compositions (i.e., shampoos, body wash, hair treating agents, such as hair removal compositions), laundry detergent compositions, agrochemical foam compositions, oil field foam compositions, firefighting foam compositions, coagulating compositions, such as treating paper making water streams, hard surface cleaning compositions. Suitable adjuncts for these compositions are well known in the art.

The present invention is further illustrated by the following examples of amine oxide monomer-containing polymeric suds enhancers (enhancing agents), provided that no observations or other statements made therein should be construed to limit the invention, unless otherwise expressly indicated in the claims appended hereto. All amounts, parts, percentages, and ratios expressed in this specification, including the claims are by weight unless otherwise apparent in context.

SYNTHESIS EXAMPLES 1. a) Synthesis of an Amine-Oxide Monomer

To a 500-ml round bottom flask, add demineralized water (149.0 g) and diethylenetriaminepentaacetic acid (0.4 g), and mix well until the powder dissolves. The pH of the resulting solution is about 2.4. Add hydrogen peroxide (50% solution, 28.7 g), and start purging with a slow stream of oxygen and heating to 60° C. At 60° C., start adding dimethylaminopropylmethacrylamide (71.9 g) over one hour to the above mixture. The temperature increases to about 65° C. and maintains there during the one-hour addition. Further hold at 65° C. for five hours, then cool the batch to room temperature. Analysis of the resulting product with both HPLC and amine oxide test, the conversion is higher than 97%. The pH of the finish product is about 7.8, and the solids is about 31.7%.

b) Polymerization of the Above Amine Oxide Monomer

To a 500-ml round bottom flask, add demineralized water (97.7 g). Under a gentle nitrogen purging, heat the water to 85° C. At 85° C., start adding the following DMAEMA monomer citrate salt solution (of pH about 5.4) and the above amine oxide monomer over 150 minutes:

| | |
|---|---|
| Dimethylaminoethylmethacrylate, DMAEMA | (95.3 g) |
| Citric acid | (63 g) |
| Demineralized water | (79.5 g) |
| Amine oxide monomer | (39.6 g) |

Simultaneously but separately to the reaction flask, add sodium persulfate solution (2.29 g in 22 g demineralized water) over 155 minutes. Maintain the temperature at 85° C. throughout the addition. Hold at 85° C. for one hour following the addition of the above two mixtures. Add another portion of sodium persulfate solution (0.11 g in 0.44 g demineralized water) all at once and then hold at 85° C. for one hour. Then cool to room temperature and let the batch stand overnight (about 16 hours). The finish polymer solution is clear and light yellow, and of a viscosity about 5,150 cps at 44% solids. The pH of the solution is about 4.6.

Experiments are repeated according the above procedure with different amounts of DMAEMA citrate salt to the amine oxide monomer, and homopolymerization of the amine oxide monomer is also done. The results are listed below.

| DMAEMA citrate: Amine oxide monomer (pH as is) | Viscosity | % solids |
|---|---|---|
| 9:1 4.6 pH | 5,150 cps | 44% |
| 7:3 4.9 pH | 4,900 cps | 39.6% |
| 1:1 5.5 pH | 1,650 cps | 35.8% |
| 0:1 6.5 pH | 155 cps | 24.5% |

2. Synthesis of DMAEMA-Amino Oxide Polymers

To a 5-liter round bottom flask equipped with a condenser, add isopropyl alcohol (2080.5 g), and start heating to reflux (about 85° C.). When the isopropyl alcohol under refluxing, start adding dimethylaminoethylmethacrylate, DMAEMA, (1598.1 g) and 2,2'-azobis(2-methylbutronitrile) isopropyl alcohol solution (16 g in 285.1 g isopropyl alcohol) simultaneously but separately over 125 minutes. Hold at refluxing temprature for one hour following the addition of the two reagents. Add a second portion of the same azo initiator isopropyl alcohol solution (1.61 g in 6.12 g isopropyl alcohol) all at once and hold for one hour. Repeat the procedure with a third portion of the azo initiator solution. Cool the batch down to room temperature following the one-hour hold with the third portion of azo initiator. Apply a vacuum (28" Hg) to distill out the isopropyl alcohol at temperature (25–33° C.). When about 706 g isopropyl alcohol distillate is obtained, add demineralized water (501 g), and re-start the distilling out isopropyl alcohol. Repeat the process with replacing the isopropyl alcohol distillate with water until there is essentially all the isopropyl alcohol is distilled out. The resulting solution is a pale yellow solution of about 38.1% solids.

To a 500-ml round bottom flask, add the above Poly (DMAEMA) solution, demineralized water (37.3 g) and diethylenetriaminepentaacetic acid (0.4 g). Heat the mixture under a gentle nitrogen purging to 32° C. Add hydrogen peroxide (50%, 22.71 g) over 5 minutes when the temperature is at 32° C. Slight reaction exotherm is observed. Hold the batch temperature at 35–40° C. for six hours. Cool the batch to room temperature and let it stand overnight (about 18 hours). The resulting Poly(DMAEMA-amine oxide) is very slight hazy, pale yellow solution of viscosity about 110 cps and of solids 29.3% at a pH of about 6.7.

Experiments are also done with a different amounts of hydrogen peroxide, thus generating a different amount of Poly(DMAEMA) to become amine oxide functionality. The results are as below.

| DMAEMA:DMAEMA-Amine oxide monomer (pH as is) | Viscosity | % solids |
|---|---|---|
| 9:1 9.1 pH | 365 cps | 29.9% |
| 7:3 9.1 pH | 155 cps | 29.8% |
| 1:1 9.0 pH | 110 cps | 29.6% |

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

The compositions of the present invention can be suitably prepared by any process chosen by the formulator, non-limiting examples of which are described in U.S. Pat. No. 5,691,297 Nassano et al., issued Nov. 11, 1997; U.S. Pat. No. 5,574,005 Welch et al., issued Nov. 12, 1996; U.S. Pat. No. 5,569,645 Dinniwell et al., issued Oct. 29, 1996; U.S. Pat. No. 5,565,422 Del Greco et al., issued Oct. 15, 1996; U.S. Pat. No. 5,516,448 Capeci et al., issued May 14, 1996; U.S. Pat. No. 5,489,392 Capeci et al., issued Feb. 6, 1996; U.S. Pat. No. 5,486,303 Capeci et al., issued Jan. 23, 1996 all of which are incorporated herein by reference.

In addition to the above examples, the cleaning compositions of the present invention can be formulated into any suitable laundry detergent composition, non-limiting examples of which are described in U.S. Pat. No. 5,679,630 Baeck et al., issued Oct. 21, 1997; U.S. Pat. No. 5,565,145 Watson et al., issued Oct. 15, 1996; U.S. Pat. No. 5,478,489 Fredj et al., issued Dec. 26, 1995; U.S. Pat. No. 5,470,507 Fredj et al., issued Nov. 28, 1995; U.S. Pat. No. 5,466,802 Panandiker et al., issued Nov. 14, 1995; U.S. Pat. No. 5,460,752 Fredj et al., issued Oct. 24, 1995; U.S. Pat. No. 5,458,810 Fredj et al., issued Oct. 17, 1995; U.S. Pat. No. 5,458,809 Fredj et al., issued Oct. 17, 1995; U.S. Pat. No. 5,288,431 Huber et al., issued Feb. 22, 1994 all of which are incorporated herein by reference.

Having described the invention in detail with reference to preferred embodiments and the examples, it will be clear to those skilled in the art that various changes and modifications may be made without departing from the scope of the invention and the invention is not to be considered limited to what is described in the specification.

What is claimed is:

1. A suds-forming and/or foam-forming detergent composition having increased suds volume and suds retention, said composition comprising:

a) an effective amount of a amine oxide monomer-containing polymeric suds enhancer having the formula;

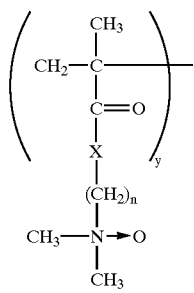

wherein X is either O or N, n is an integer from 1 to 10 and wherein said amine oxide monomer-containing polymeric suds enhancer has an average molecular weight of from about 1,000 to about 2,000,000 daltons b) an effective amount to clean a surface in need of cleaning of a detersive surfactant; and c) the balance carriers and other adjunct ingredients;

provided that a 10% aqueous solution of said suds-forming and/or foam-forming composition has a pH of from about 4 to about 12.

2. A composition according to claim 1 wherein said amine oxide monomer-containing polymeric suds enhancer has an average molecular weight of from about 5,000 to about 1,000,000 daltons.

3. A composition according to claim 2 wherein said amine oxide monomer-containing polymeric suds enhancer has an average molecular weight of from about 10,000 to about 750,000 daltons.

4. A composition according to claim 1 wherein said amine oxide monomer-containing polymeric suds enhancer further comprises one or more other monomeric units selected from the group consisting of cationic monomeric units, anionic monomeric units, nonionic monomeric units, hydrophobic group-containing monomeric units, hydrophilic group-containing monomeric units, hydroxyl-containing monomeric units and mixtures thereof.

5. A composition according to claim 4 wherein said amine oxide monomer-containing polymeric suds enhancer comprises a cationic monomeric unit of the formula:

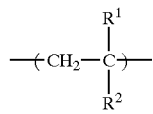

wherein:

$R^1$ is H or an alkyl having 1 to 10 carbon atoms, $R^2$ is a moiety selected from the group consisting of

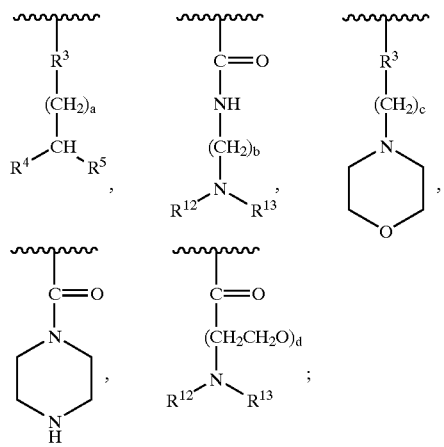

wherein $R^3$ is selected from the group consisting of a is an integer from 0 to 16;

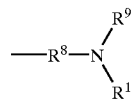

b is an integer from 2 to 10;

c is an integer from 2 to 10;

d is an integer from 1 to 100;

$R^4$ and $R^5$ are independently selected from the group consisting of —H, and $R^8$ is independently selected from the group consisting of a bond or an alkylene having 1 to 18 carbon atoms;

$R^9$ and $R^{10}$ are independently selected from the group consisting of —H, alkyl having 1 to 8 carbon atoms, and an olefin chain having 2 to 8 carbon atoms;

$R^{12}$ and $R^{13}$ are independently selected from the group consisting of H and alkyl having from 1 to 8 carbon atoms;

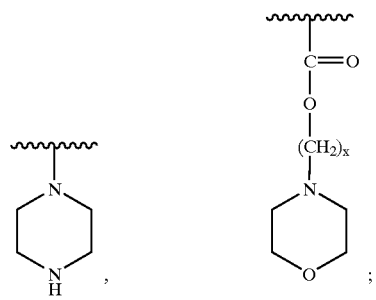

wherein x is an integer from 2 to 10.

6. A composition according to claim 5 wherein $R^1$ has the formula:

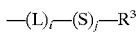

$$-(L)_i-(S)_j-R^3$$

wherein L is a linking unit independently selected from the following:

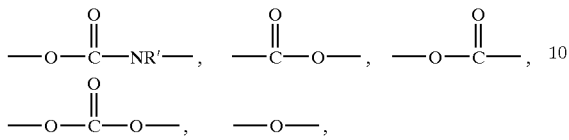

and mixtures thereof; R' is independently hydrogen, $C_1$–$C_4$ alkyl, and mixtures thereof or R' and S can form a heterocycle of 4 to 7 carbon atoms, optionally containing other hetero atoms and optionally substituted; $R^3$ is independently selected from —$CO_2M$, —$SO_3M$, —$OSO_3M$, —$CH_2P(O)(OM)_2$, —$OP(O)(OM)_2$, units having the formula:

$$-CR^8R^9R^{10}$$

wherein each $R^8$, $R^9$, and $R^{10}$ is independently selected from the group consisting of hydrogen, —$(CH_2)_m R^{11}$, and mixtures thereof, wherein $R^{11}$ is —$CO_2H$, —$SO_3M$, —$OSO_3M$, —$CH(CO_2H)CH_2CO_2H$, —$CH_2P(O)(OH)_2$, —$OP(O)(OH)_2$, and mixtures thereof; provided that one $R^8$, $R^9$, or $R^{10}$ is not a hydrogen atom; $R^2$ has the formula:

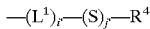

$$-(L^1)_i-(S)_{j'}-R^4$$

wherein $L^1$ is a linking unit independently selected from the following:

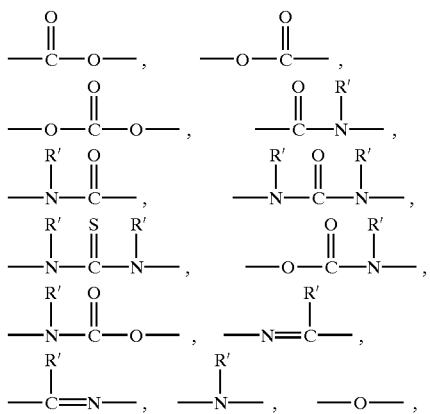

and mixtures thereof; wherein R' is independently hydrogen, $C_1$–$C_4$ alkyl, and mixtures thereof or alternatively R' and S can form a heterocycle of 4 to 7 carbon atoms, optionally containing other hetero atoms and optionally substituted; $R^4$ is independently selected from amino, alkylamino carboxamide, 3-imidazolyl, 4-imidazolyl, 2-imidazolinyl, 4-imidazolinyl, 2-piperidinyl, 3-piperidinyl, 4-piperidinyl, 1-pyrazolyl, 3-pyrazoyl, 4-pyrazoyl, 5-pyrazoyl, 1-pyrazolinyl, 3-pyrazolinyl, 4-pyrazolinyl, 5-pyrazolinyl, 2-pyridinyl, 3-pyridinyl, 4-pyridinyl, piperazinyl, 2-pyrrolidinyl, 3-pyrrolidinyl, guanidino, amidino, and mixtures thereof; each S is independently selected from $C_1$–$C_{12}$ linear alkylene, $C_1$–$C_{12}$ branched alkylene, $C_3$–$C_{12}$ linear alkenylene, $C_3$–$C_{12}$ branched alkenylene, $C_3$–$C_{12}$ hydroxyalkylene, $C_4$–$C_{12}$ dihydroxyalkylene, $C_6$–$C_{10}$ arylene, $C_8$–$C_{12}$ dialkylarylene, —$(R^5O)_k R^5$—, —$(R^5O)_k R^6(OR^5)_k$—, —$CH_2CH(OR^7)CH_2$—, and mixtures thereof; $R^5$ is $C_2$–$C_4$ linear alkylene, $C_3$–$C_4$ branched alkylene, and mixtures thereof; $R^6$ is $C_2$–$C_{12}$ linear alkylene, and mixtures thereof; $R^7$ is hydrogen, $C_1$–$C_4$ alkyl, and mixtures thereof; M is hydrogen or a water soluble cation; i is 0 or 1; i' is 0 or 1; j is 0 or 1; j' is 0 or 1; k is from 1 to 20; and m is from 0 to 10.

7. A composition according to claim 6 wherein I and j are each equal to 0.

8. A composition according to claim 7 wherein R is $C_1$–$C_4$ linear alkylene, $C_1$–$C_4$ branched alkylene, and mixtures thereof; $R^3$ —$CO_2M$, $L^1$ has the formula:

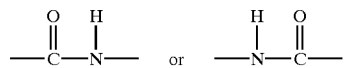

S is $C_2$–$C_4$ linear alkylene; $R^4$ is alkylamino having the formula:

$$-N(R^{11})_2$$

wherein each $R^{11}$ is independently hydrogen, $C_1$–$C_4$ alkyl, and mixtures thereof or the two $R^{11}$ can form a heterocycle of 4 to 8 carbon atoms, optionally containing other hetero atoms and optionally substituted; M is hydrogen; x is 1; y is 1, z is 1.

9. A composition according to claim 5 wherein $R^1$ is —$CO_2H$, $R^2$ is selected from the group consisting of:

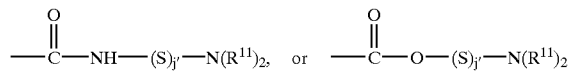

wherein $R^{11}$ is hydrogen, methyl, and mixture thereof; S is $C_2$–$C_6$ linear alkylene; j' is 1.

10. A composition according to claim 9 wherein $R^2$ is selected from the group consisting of:

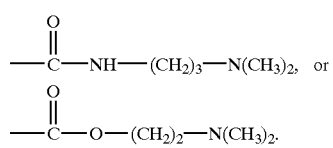

11. A composition according to claim 1, wherein said other adjuncts ingredients is selected from the group consisting of: soil release polymers, polymeric dispersants, polysaccharides, abrasives, bactericides, tarnish inhibitors, builders, enzymes, opacifiers, dyes, perfumes, thickeners, antioxidants, processing aids, other suds boosters, buffers, antifungal or mildew control agents, insect repellants, anticorrosive aids, and chelants.

12. A composition according to claim 1, further comprising an enzyme selected from the group consisting of protease, amylase, mannanase, xyloglucanase, and mixtures thereof.

13. A composition according to claim 1, wherein said detersive surfactant (b) is selected from the group consisting of amine oxides, polyhydroxy fatty acid amides, betaines, sulfobetaines, alkyl polyglycosides, alkyl ethoxylates, and mixtures thereof.

14. The composition according to claim 1 wherein the composition is a personal care composition.

15. The composition according to claim 1 wherein the composition is a laundry detergent composition.

16. The composition according to claim 1 wherein the composition is a hard surface cleaning composition.

17. The composition according to claim 1 wherein the composition is an agrochemical foaming composition.

18. The composition according to claim 1 wherein the composition is an oil-field foaming composition.

19. The composition according to claim 1 wherein the composition is a fire-fighting foaming composition.

20. The composition according to claim 1 wherein the composition is a liquid dishwashing composition.

21. A composition according to claim 1 wherein the amine oxide monomer-containing polymeric suds enhancer further comprises:

a) a monomeric unit having the formula:

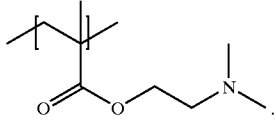

* * * * *